United States Patent [19]

Albright et al.

[11] 4,038,030

[45] July 26, 1977

[54] PROFILE ANALYSIS PACK AND METHOD

[75] Inventors: Bill E. Albright, Diamond Bar, Calif.; Michael D'Aquino; Zindel H. Heller, both of Miami, Fla.

[73] Assignee: American Hospital Supply Corporation, Evanston, Ill.

[21] Appl. No.: 566,921

[22] Filed: Apr. 10, 1975

[51] Int. Cl.² .................... G01N 33/16; G01N 21/24
[52] U.S. Cl. .............................. 23/230 B; 23/253 R; 23/259; 356/246
[58] Field of Search ............ 23/253 R, 230 R, 230 B, 23/259, 292; 356/246

[56] References Cited

U.S. PATENT DOCUMENTS

| | | | |
|---|---|---|---|
| 3,476,515 | 11/1969 | Johnson et al. | 23/230 |
| 3,497,320 | 2/1970 | Blackburn et al. | 23/230 |
| 3,556,731 | 1/1971 | Martin | 23/253 |
| 3,620,678 | 11/1971 | Guigan et al. | 23/253 |
| 3,689,224 | 9/1972 | Agnew et al. | 23/253 TP |
| 3,697,227 | 10/1972 | Goldstein et al. | 23/253 TP |
| 3,770,382 | 11/1973 | Carter et al. | 23/253 R |
| 3,799,742 | 3/1974 | Coleman | 23/253 R |

*Primary Examiner*—R.E. Serwin
*Attorney, Agent, or Firm*—Tilton, Fallon, Lungmus, Chestnut & Hill

[57] ABSTRACT

A profile analysis reaction pack and related apparatus are disclosed, along with a method for simultaneously mixing, heating and reacting selected test reagents with multiple dilutions of a sample of body fluid to obtain a profile of the physiological condition of a given organ system. Each pack takes the form of a laminated card having a relatively rigid flat panel of transparent material secured to an opaque resilient panel, the resilient panel being preformed to define a plurality of generally semi-cylindrical reaction chambers disposed between the respective panels. During a profile test procedure, a sample of the body fluid to be tested is withdrawn from a storage chamber in the same pack and each reaction chamber is then injected with a diluted portion of the sample fluid. Temperature control is achieved by bracing the rigid panel of the pack against a fixed heated platen and by contacting the generally semi-cylindrical wall portion of each reaction chamber with a movable heated platen. Because of the shape of each movable platen, the configuration and resilience of the reaction chamber wall which it engages, and the limited reciprocation of the movable platen, the reagent in each reaction chamber is rapidly dissolved (if originally in powder or tablet form) and the reactants are agitated and circulated to insure thorough mixing and complete reaction. Thereafter, with the pack held between heated platens, the extent of reaction in each chamber is optically determined by directing an oblique light beam towards the transparent wall of each chamber and then measuring the front surface fluorescence emitted through the same wall. Indicia representing the results of each test are applied directly to a card portion of the pack (which also bears indicia identifying the test, patient, etc.) and such card portion is then separated from the rest of the pack to provide a permanent record of the profile results.

20 Claims, 16 Drawing Figures

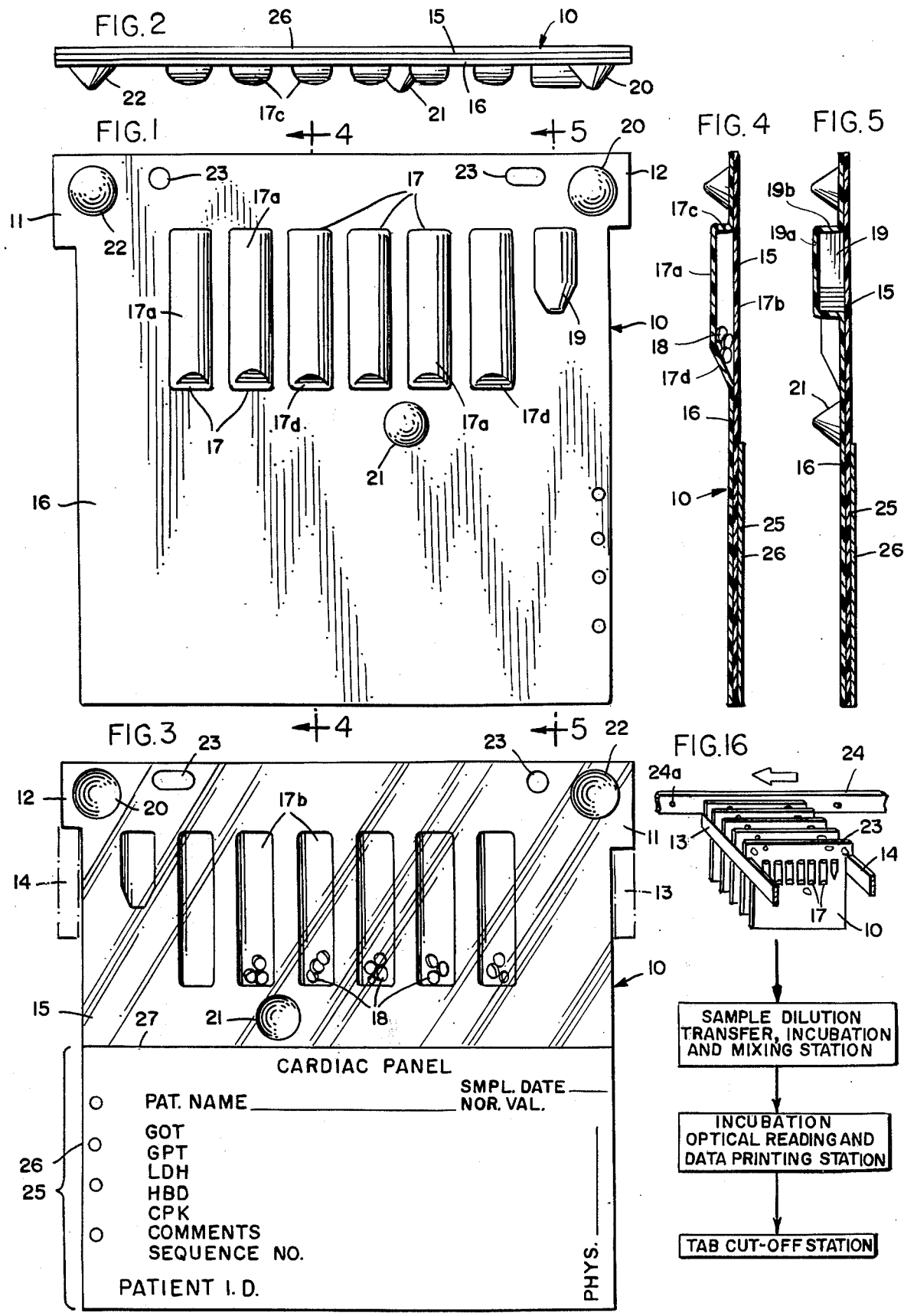

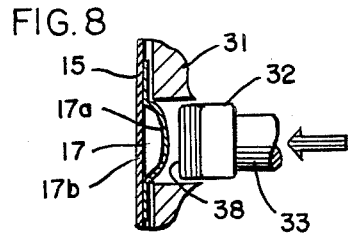
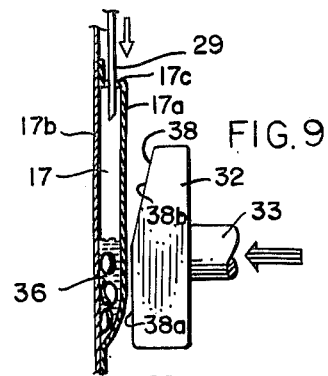
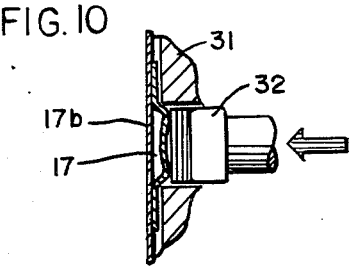
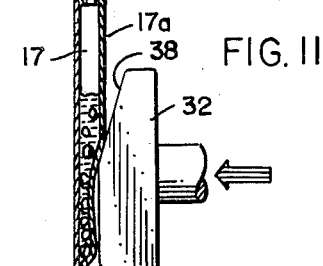
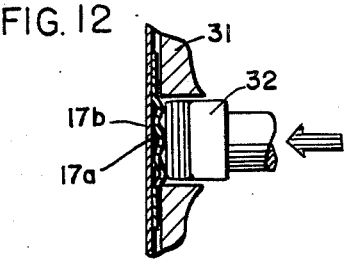
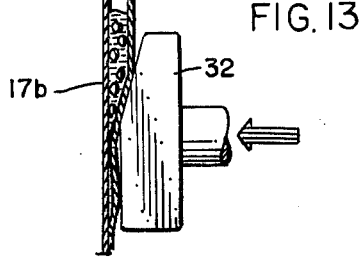
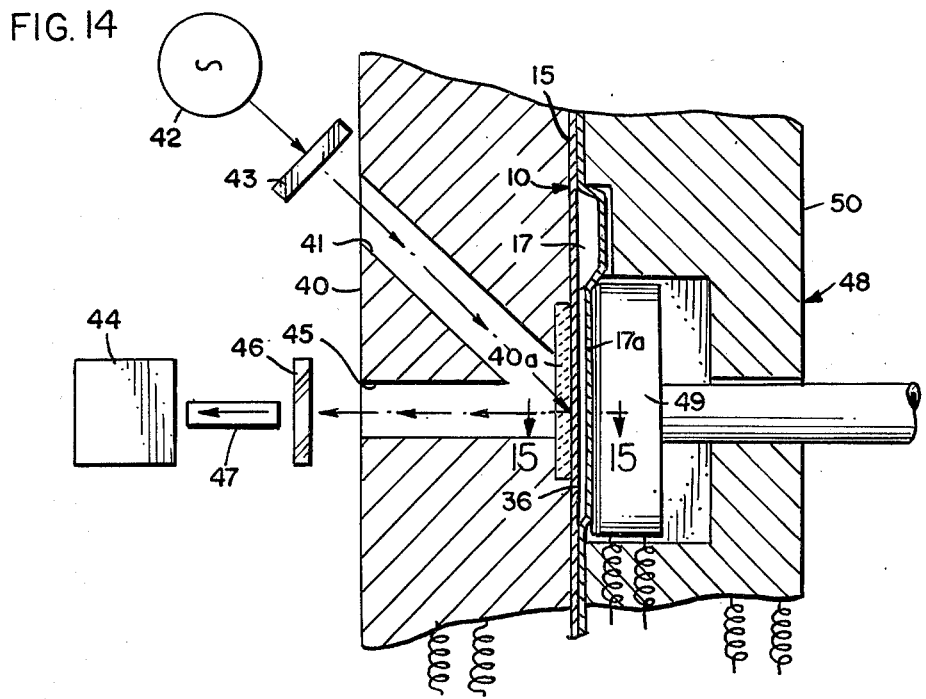

PROFILE ANALYSIS PACK AND METHOD

BACKGROUND

While disposable test packs for use in automatic anaylis equipment have been known in the past, such packs have presented difficulties in construction and operation whenever their use as disposable cuvettes has been a design requirement. Typically, such a pack provides a single reaction chamber which also doubles as a cuvette through which light must be passed when an optical reading is taken. Not only must the dimensions and optical quality of the opposing transparent walls be precisely controlled during manufacture, but the spacing between those walls must be carefully maintained when the pack is used as a cuvette. Variations in such spacing which might be occasioned, for example, by the highly pliable nature of the material from which the bag-like chamber is formed, could have a substantial effect on the absorbence values and that in turn could result in possible errors in diagnosis. Such problems would be multiplied if the teachings of the prior art were embodied in a pack having multiple chambers for simultaneously performing a number of tests, a possible reason why disposable packs for use in conducting profile analyses have been generally unknown and unavailable in the past.

The state of the art is further indicated by the following U.S. Pats. and the references cited therein: Nos. 3,770,382, 3,476,515, 3,775,595, 3,504,376, 3,497,320, 3,554,705, 3,526,480, 3,477,821, 3,477,822, 3,480,398, 3,480,399, 3,545,934, 3,545,935, 3,582,285, 3,582,283, 3,703,336, 3,718,439, 3,540,858, 3,540,857, 3,540,856, and 3,532,470.

SUMMARY OF THE INVENTION

It is an object of this invention to overcome the aforementioned disadvantages and defects of the prior art and, in general, to provide a disposable reaction pack which is adapted for use in simultaneously performing multiple clinical tests on a sample of body fluid, and which has a plurality of reaction chambers, each of which is capable of performing a cuvette-like function without requiring light to pass therethrough during an optical reading.

Front-surface fluorometry is a technique well known in the art for measuring the extent of reaction, or the rate of reaction, in enzymatic tests and other diagnostic tests commonly performed in clinical laboratories; however, such technique has not to our knowledge been utilized in the past to overcome the problems described above in the construction and use of disposable test packs. Therefore, one aspect of this invention lies in the discovery that front-surface fluorometry is particularly useful in clinical testing procedures employing inexpensive disposable test packs, especially packs having multiple reaction chambers in which a plurality of tests may be performed simultaneously on dilutions of a single sample of body fluid. In the use of a pack embodying this invention, ultraviolet light is directed at an oblique angle towards a rigid optically-transparent wall of each reaction chamber and the intensity of fluoroscent light emitted through the same wall (that is, from the "front surface" of the encapsulated fluid against which the ultraviolet light impinges) is then measured as a direction indication of the extent of reaction. Although, in a preferred embodiment of the invention, the pack has a plurality of such chambers, the same transparent panel serves as a front wall for all of those chambers and, consequently, relatively low fabrication costs, and disposability of a multiple-test pack, may be achieved.

In brief, the pack includes a relatively rigid panel which is both flat and transparent and a resilient or flexible panel which is opaque and which is preformed to define (in conjunction with the transparent panel) a series of generally semi-cylindrical reaction chambers. The resilient panel is also provided with an additional deformation or recess which, in combination with the rigid panel, defines a chamber for storing a sample of serum or other body fluid. The pack therefore takes the form of a multiple-chambered card. The card extends beyond the series of chambers to provide means for receiving indicia concerning the identity of the patient, the nature of the tests, the results of those tests, and whatever other information is deemed necessary or desirable. While the pack has been referred to as a "disposable" pack, it is intended that the indicia-bearing portion of the pack be severed and retained for future reference and that only the chamber-providing portion of the pack be discarded after the tests are completed.

It is significant that the rear panel defining the semi-cylindrical portion of each of the reaction chambers is semi-rigid but nevertheless resilient in nature, in contrast to being pliant and incapable of resisting distoring forces and of returning to its original configuration to relieve internal stresses arising from deformation. The resilient wall must be stiff enough to resist collapse when engaged and pierced by a tubular injector at the beginning of a dissolving and mixing operation. During such an operation, each reaction chamber is engaged by a heated movable platen which alternately stresses and deforms the arcuate side wall of the reaction chamber and then retracts to permit the deformed wall portion to return to its original unstressed configuration. Solid reagent is thereby crushed and rapidly dissolved in the diluted body fluid previously injected into each reaction chamber, and continued reciprocation insures that the reactants are circulated and thoroughly intermixed. During such mixing and heating operation, the flat transparent panel of the pack is braced against a fixed platen which is also heated. Precise control over the reaction temperature in each of the chambers may therefore be maintained.

When the test reactions have progressed to the point where readings are to be taken, the pack is advanced to an optical analysis station where it is again held between heated platens; however, the fixed platen at such station is provided with openings which align with intermediate portions of the transparent wall of each reaction chamber, and the movble platen has a horizontally convex surface for engagement with the flexible wall of each chamber. Ultraviolet light is directed through such openings and emitted fluorescence is measured in the manner already indicated. The results of the tests are imprinted on the tab or card portion of the pack and that portion is then servered from the remainder of the pack for later reference.

Other objects and advantages of the invention will become more apparent as the specification proceeds.

DRAWINGS

FIG. 1 is a rear view of a multiple-chambered profile test pack embodying the present invention.

FIG. 2 is a top view of the pack.

FIG. 3 is a front elevational view of the pack.

FIGS. 4 and 5 are vertical sectional views taken along lines 4 and 5, respectively, of FIG. 1.

Figure 6:
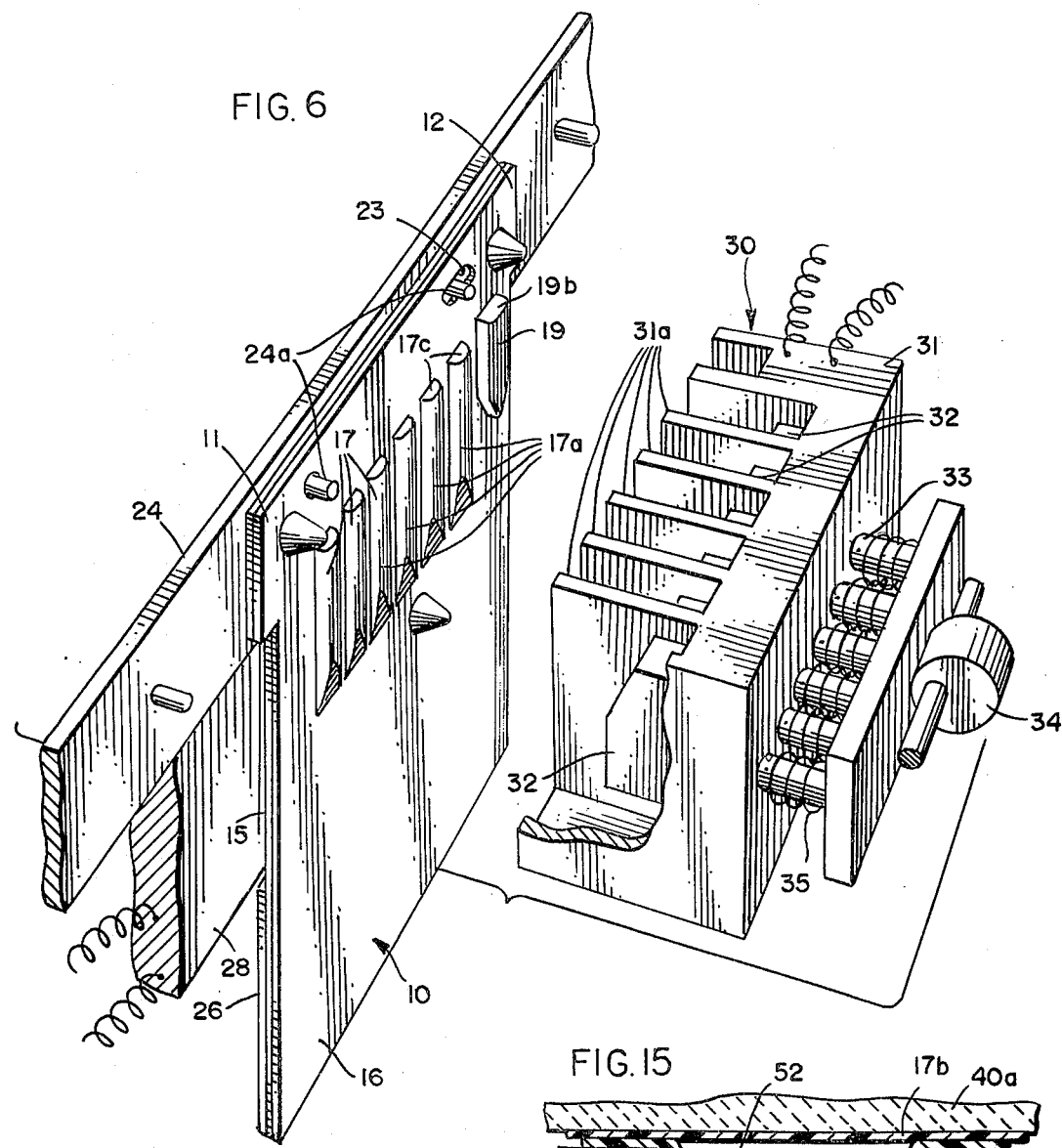

FIG. 6 is a fragmentary perspective view, in somewhat schematic form, illustrating a profile test pack supported in position prior to injection of liquid into the reaction chambers and engagement by the movable platens which heat and mix the reactants in each chamber.

Figure 7:
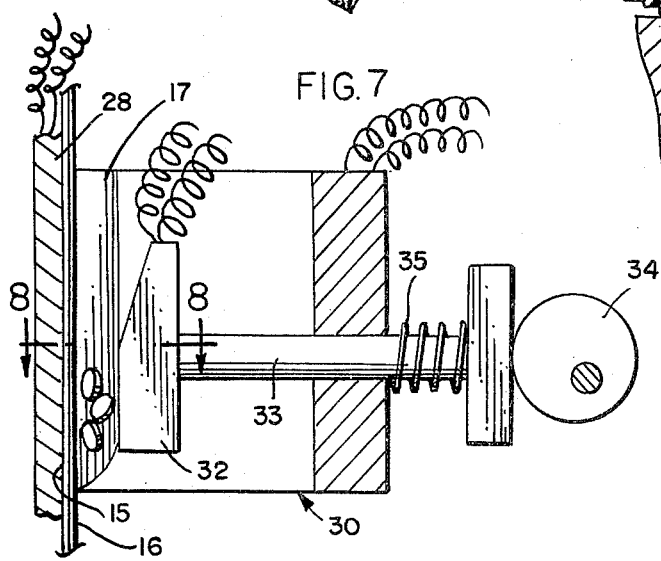

FIG. 7 is a somewhat schematic vertical sectional view illustrating a movable platen of FIG. 6 after it has been shifted into operative position.

FIGS. 8 and 9 are fragmentary horizontal and vertical sections views, respectively, showing the condition of a reaction chamber and its contents at the beginning of the dissolving, crushing, mixing and heating steps, and prior to engagement by the movable platen.

FIGS. 10 and 11 are views similar to FIGS. 8 and 9 but showing the convex resilient wall of the reaction chamber partially deformed by the movable platen.

FIGS. 12 and 13 are views similar to FIGS. 10 and 11 but showing the condition of the reaction chamber when the movable platen is fully extended.

FIG. 14 is a fragmentary and somewhat schematic vertical sectional view illustrating the manner in which a pack is supported when an optical reading is taken using frontsurface fluorometry.

Figure 15:
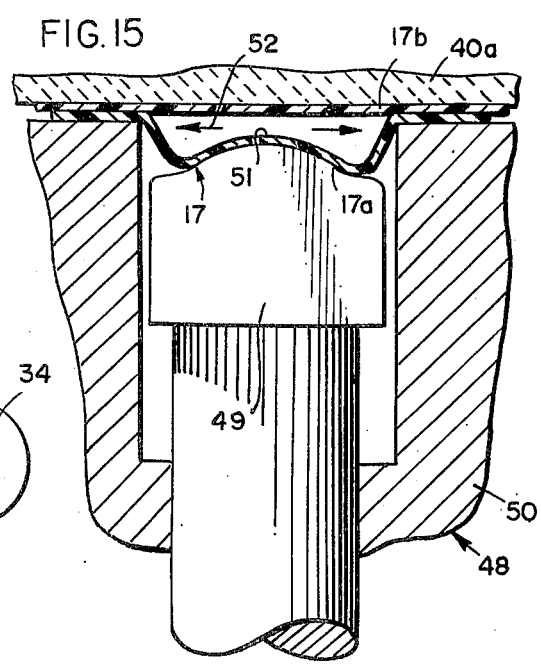

FIG. 15 is an enlarged horizontal sectional view illustrating the change in configuration which arises when the flexible wall of the chamber is deformed by the movable platen at the optical reading station.

FIG. 16 is a diagram showing the sequence of steps in the processing of a profile test pack embodying this invention.

DETAILED DESCIPTION

Referring to the drawings, the numeral 10 generally designates a test pack which is in the general shape of a rectangular card. The card is intended to be supported in substantially vertical condition and, for that purpose, is provided at its upper corners with a pair of laterally-projecting ear portions 11 and 12. It will be observed that ear 11 has vertical dimensions greater than ear 12 to prevent a user from inadvertently loading a pack in reverse direction upon magazine support rails 13 and 14 (FIGS. 3 and 13).

The pack includes a pair of pair of panels 15 and 16 which are sealed together by heat fusion, adhesive, or any other suitable means. Panel 15, which constitutes the front panel of the pack, is transparent and relatively rigid. Polymers of methylpentene have been found particularly effective but any other relatively rigid plastic which is transparent (especially to ultraviolet light) may be used. It is to be noted that panel 15 is flat or planar, in contrast to panel 16 which is formed to define the generally semi-cylindrical wall portions 17a of a series of reaction chamber 17.

Each reaction chamber is formed not only by semi-cylindrical wall portion 17a of panel 16 but also by transparent wall portion 17b of planar panel 15 (FIGS. 3 and 8). Each chamber is also closed at its opposite ends, the top wall portion 17c extending in a plane generally normal to the axis of the vertically-elongated reaction chamber, and bottom wall 17d preferably sloping so as to merge smoothly at obtuse angles with semi-cylindrical wall 17a and also with the planar portion of panel 16 below each reaction chamber. The reaction chambers are normally completely sealed and, except for one chamber which may be used for control purposes, contain measured quantities of reagents 18. To facilitate storage, such reagents are preferably in solid form and, while the reaction chambers are shown as containing a plurality of pellets or tablets, it is to be understood that solid reagent or reagents may be provided in each chamber as a single tablet or, alternatively, in granular or powder form.

The selection of reagents depends upon the test reactions to be performed, such reagents and reactions being published and known in the art. For example, where a cardiac profile is sought, the selected tests might be for lactate dehydrogenase (LDH), glutamic-oxalacetic transaminase (GOT), glutamic-pyruvic transaminase (GPT), alphahydroxybutyrate dehydrogenase (HBDH), and creatine phosphokinase (CPK), and the reagents might be selected so that in each case the fluorescing reaction product would be dihydronicotinamide adenine dinucleotide (NADH$_2$). For the LDH test, the reagent would consist essentially of lactate and nicotinamide adenine dinucleotide (NAD), whereas for the HGDH test, the reagent would consist essentially of NAD and alpha-hydroxbutyrate. The reactions and principal reactants of each of the tests in such a cardiac profile may be given, by way of example, as follows:

1. LDH: Lactate Dehydrogenase

Lactate + NAD $\underset{\longleftarrow}{\overset{LDH}{\longrightarrow}}$ Pyruvate + NADH 2. GOT: Glutamic-Oxalacetic Transaminase

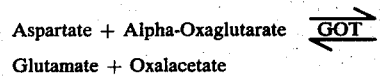

Aspartate + Alpha-Oxaglutarate $\underset{\longleftarrow}{\overset{GOT}{\longrightarrow}}$ Glutamate + Oxalacetate

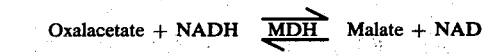

Oxalacetate + NADH $\underset{\longleftarrow}{\overset{MDH}{\longrightarrow}}$ Malate + NAD 3. GPT: Glutamic-Pyruvic Transaminase

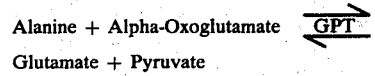

Alanine + Alpha-Oxoglutamate $\underset{\longleftarrow}{\overset{GPT}{\longrightarrow}}$ Glutamate + Pyruvate

Pyruvate + NADH $\underset{\longleftarrow}{\overset{LDH}{\longrightarrow}}$ Lactate + NAD 4. HBDH: Alpha-Hydroxybutyrate Dehydrogenase

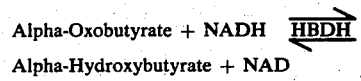

Alpha-Oxobutyrate + NADH $\underset{\longleftarrow}{\overset{HBDH}{\longrightarrow}}$ Alpha-Hydroxybutyrate + NAD 5. CPK: Creatine Phosphokinase

Creatine + ATP $\underset{\longleftarrow}{\overset{CPK}{\longrightarrow}}$ Creatine Phosphate + ADP

ADP + PEP $\underset{\longleftarrow}{\overset{PK}{\longrightarrow}}$ ATP + Pyruvate

Pyruvate + NADH $\underset{\longleftarrow}{\overset{LDH}{\longrightarrow}}$ Lactate + NAD Similarly, for a liver profile those tests would be selected which would reveal the condition of that organ or organ system, the information pertaining to the appropriate tests being available in the medical and scientific literature. Reference is made, for example, to Ricterich, Clinical Chemistry, S. Karger (1969). Since the particular tests and reagents selected in the use of the pack do not of themselves constitute a part of this invention, and since such reactions and reagents are known in the art, further description is believed unnecessary herein. It is to be pointed out, however, that the word "profile" is used herein to mean a group of clinical tests intended to provide information concerning the condition of a given organ or organ system (e.g., heart, kidney, liver, pancreas) or of a given syndrome (e.g., bone disease, blood disease, etc.). The examples given above are only illustrative of a wide variety of diagnostic tests that may be used in the method and apparatus of this invention.

A characteristic of panel 16, and particularly of the horizontally-convex wall portions 17b formed in that panel, is that such wall portions will tend to return to their generally semi-cylindrical condition following deformation (as shown in FIGS. 10 through 13) and the subsequent removal of the deforming forces. Each wall portion 17a is preformed and, although flexible, resists deformation. Upon forceable deformation in the manner indicated, wall portion 17a develops stresses and tensions which tend to restore the original configuration as soon as the deforming forces are removed. A variety of commercially-available single-ply and laminated plastic materials may be employed to achieve the necessary flexibility and resilience, along with other desired properties such as chemical stability, inertness, gas impermeability, and opacity. Laminates of nylon, polyethylene and pigmented Surlyn (an ionic monomer marketed by E. I. du Pont de Nemours & Co., Inc., Wilmington, Del.) have been found particularly effective. In one embodiment, a nylon-polyethylene-Surlyn film laminate having a thickness of 0.01 inches was suitable but it is believed apparent that such thickness might vary considerably depending upon the particular resilient semi-rigid plastic material or materials selected for use. As indicated, the material of rear panel 16 should also be opaque to prevent light from passing through the reaction chamber and to avoid light interference or "crosstalk" between adjacent reaction compartments.

In addition to the reaction chambers 17, the pack is provided with a sample chamber 19. The sample chamber is preformed in flexible panel 16 and has an outer wall 19a and a top wall portion 19b. The top wall portion is generally horizontal (i.e., normal to the vertical axis of the chamber) and, prior to use, the sample chamber is both sealed and empty (except for the presence of sterile gas). Protuberances 20–22 are formed in the flexible panel 16 and project outwardly from that panel beyond the limits of chambers 17 and 19 to help protect those chambers against inadvertent compression and to serve as spacers between adjacent packs when a number of such packs are supported upon magazine rails 13 and 14. Along its upper edge, the pack is provided with openings 23 to receive the supporting lugs of pins 24a of a conveyor strap 24 (FIGS. 6 and 16).

Means are provided beneath all of the chambers 17 and 19 for receiving appropriate indicia concerning the identity of the patient, the nature of the tests, the results of such test, and other desired information, some of which would be applied manually prior to automatic processing of the pack and other of which would preferably be applied automatically through operation of the analyzing equipment following completion of the tests and automatic optical measurement of the results. In the illustration given, the means comprises a lower tab or card portion 25 of the pack which is formed integrally with panels 15 and 16 but which, in addition, bears a rectangular sheet 26 formed of paper or other suitable material capable of receiving and retaining such indicia. It is to be understood that if the material of panel 15 (or panel 16) is such that ink imprints or other indicia may be received and securely retained, then the use of a paper layer or sheet 26 may be avoided. Conversely, where multiple copies of the sheet bearing the data are desired, a plurality of superimposed sheets with impression-transferring coatings therebetween may be adhesively attached to panel 15. As shown in FIG. 3, sheet 26 is preprinted to indicate the nature of the test and to provide blanks for receiving patient identification and test data. The upper edge 27 of the sheet extends along a line of serverance so that following completion of a testing procedure the tab section 25 of the pack may be severed from the remainder of that pack with the lower portion being retained for future reference and the upper portion being discarded (FIG. 13).

Information concerning the indentity of the patient, the name of the physician, and the date of the test (sampling date) is written on the face of the pack at the time that a sample of body fluid is injected into sample chamber 19. The needle of the syringe in which the sample is drawn is simply inserted through the flat top wall 19b of chamber 19 and the sample fluid is then injected until the chamber is substantially filled. Thereafter, the pack is supported upon the rails 13, 14 and advanced towards conveyor strap 24 until lugs 24a enter openings 23 and carry the suspended card in the direction of intermittent movement of the conveyor strap. While it is believed evident that such operations would be performed automatically as part of the functioning of an automated analyzer, at least some of the steps might be carried out manually.

The conveyor strap 24 advances the pack to a sample dilution and transfer station represented in FIGS. 16 and 6–13. Referring to FIG. 6, it will be observed that the pack is supported with transparent panel 15 disposed against the vertical surface of a fixed platen 28 which is heated electrically or by any other suitable means to the desired temperature (preferably 37.5° C.) for performing the chemical reactions. Thereafter, a diluter, which may be similar in operation and structure to the diluten disclosed in U.S. Pat. No. 3,446,400, and which is provided with a suitable probe or needle 29 for piercing the plastic top wall 19b of the sample chamber, withdraws measured portions of the sample and discharges those portions with measured quantities of suitable diluent (ordinarily distilled water) into each of the reaction chambers 17. Entry into the reaction chambers is made by simply piercing the horizontal top wall 17c thereof, the flat horizontal nature of such walls, and particularly their self-sustaining semi-rigid property, facilitating penetration by a generally vertically descending probe or needle (FIG. 9). The stiffness of each top wall, and the fact that it extends in a plane generally normal to the direction of movement of the probe (which in turn travels longitudinally of the elongated chamber), contribute significantly in preventing the needle from glancing off of, and not penetrating, the top wall.

Dissolving of the reagents in the reaction chambers, and thorough mixing of the reactants, is achieved by cyclically deforming the semi-cylindrical wall portion 17a of each reaction chamber 17 in the manner most clearly illustrated in FIGS. 8–13. The means for applying and releasing such distorting forces comprises a movable platen assembly generally designated by the numeral 30 in FIG. 6. That assembly includes a heated frame 31 having a series of vertical partitions 31a oriented to engage the pack 10 on opposite sides of each reaction chamber 17 when the entire assembly is advanced into engagement with the pack. Between each such partition 31a is a heated reciprocable shoe or platen 32 mounted upon a shaft 33 which is alternately advanced and retracted by power-driven eccentric 34 and return spring 35 (FIG. 7). Each platen 32 reciprocates between a retracted position (FIG. 8) and an extended position (FIGS. 12-13). When the movable platen 32 is retracted, the semi-cylindrical wall 17a of each reaction chamber 17 is permitted to return to its normal untensioned semi-cylindrical configuration although if desired the platen need not retract out of contact with that wall. If spacing exists, it may be greater or less than as shown in FIGS. 8-9 although minimal spacing is preferred because platen 32, in addition to cyclically deforming wall 17a, also tramsmits heat to the reaction chamber to assist in maintaining the reactants at a predetermined temperature.

As shown in FIG. 9, the volume of the reactants 36 only partially fills reaction chamber 17 when wall 17a is in its normal undeformed state. Preferably, the liquid occupies less than one half of the total volume of the chamber, the optimum amount being approximately one third (as shown). When wall 17a is deformed by the extended platen 32, the level of the liquid rises in the chamber (FIGS. 10-13). Air displaced from the chamber is vented through opening 37 previously formed when the diluted sample was injected through the top wall 17c.

Each movable platen 32 has a face 38 which, in the embodiment illustrated, includes a generally planar (vertical) lower portion 38a and a rearwardly and upwardly sloping upper portion 38b. The lower portion 38a has a vertical dimension less than one half tht of each reaction chamber, the preferred dimension being about one third of height of that chamber, and is oriented to engage only the lower part of the chamber's flexible wall 17a (FIGS. 10-13). As the movable platen advances to deform the wall, reagent tablets in the chamber are crushed and fluid in the chamber's lower portion is displaced upwardly; however, the sloping upper surface 38b of the platen provides a relief zone in which the wall remains undeformed (or less deformed), thereby permitting the displaced fluid to be accommodated within the upper portion of the chamber even when the platen is fully extended (FIG. 13). When the platen retracts and the wall 17a is permitted to return to its normal untensioned state, the direction of flow is reversed. The contents of the chamber are therefore circulated and agitated, effectively dissolving the reagent (if a solid reagent is used) and thoroughly intermixing the reactants while at the same time maintaining those reactants at a uniform selected temperature.

It is to be noted that even when the movable platen is fully advanced or extended, the closest distance between the two platens is still appreciably greater than the combined thickness of walls 17a and 17b (FIGS. 12-13). While wall 17a is momentarily re-shaped, it is not creased, sharply buckled, or permanently deformed. Referring to FIGS. 12 and 13, it will be observed that the resilient wall assumes an undulating configuration within the space between the fixed platen and the lower portion 38a of the movable platen's contact surface 38. The minimum distance between the platens when the movable platen is advanced may vary considerably depending on the material of the pack and its thickness; however, where the reagent is packaged in tablet form (as shown), such distance should be less than the combined thickness of walls 17a and 17b plus the smallest dimension of the tablets disposed within the chamber, thereby insuring that the tablets will in fact be crushed as the movable platen reciprocates.

When the predetermined incubation or reaction period has expired, the mixing step is discontinued and the pack is advanced by conveyor strap 24 to an optical reading and data printing station represented diagrammatically in FIG. 16 and shown somewhat schematically in FIG. 14. Once again the flat transparent panel of the pack is urged tightly against a heated stationary platen by means of a second platen assembly which is also heated. The stationary platen 40 is provided with a transparent (glass) window 40a which has a surface flush with the remaining surface of that platen. As shown in FIG. 14, the fixed platen is provided with passages 41 for directing ultraviolet light emitted from source 42 and passing through optical filter 43 along an oblique path towards window 40a and the intermediate portion of each reaction chamber. The light passes through the rigid transparent panel 15 and impinges on the front surface of the fluid 36 supported within the chamber. The front surface fluorescence of that liquid is then detected by a conventional photodetector 44, the emitted fluorescence passing through passage 45 in the fixed platen, filter 46, and fiber optic cable or bundle 47.

The movable platen assembly 48 is similar to the assembly 30 already described except that heated shoes or platens 49 do not reciprocate as the optical reading step is carried out and the contact surface of such platens is different. Frame 50, which is substantially identical to previously-described frame 31, is simply shifted into position to force the pack 10 against the fixed platen and movable platens 49, each with a developed contact surface 51 (FIG. 15). Surface 51 has a convex transverse (horizontal) curvature, preferably of smaller radius than the radius of curvature of wall 17a when that wall is in an unflexed or unstressed condition. As the movable platen advances to deform wall 17a, fluid in the central portion of the chamber is forced laterally as indicated by arrows 52. The result is that the fluid is redistributed to insure more uniform temperature control and the rigid wall 17b is maintained in more uniform forceful engagement with the stationary platen throughout the critical area. It will also be noted that reproducibility and uniformity are assured because that portion of wall 17a engaged by the movable platen is deformed in a predetermined, definite, and uniform manner. Specifically, that wall portion (the lower one half to two thirds of wall 17a) completely engages the movable platen to help achieve consistent reproducible operation.

It will be noted that since the light from source 42 impinges on the liquid contained in each chamber 17 well above the bottom of that chamber, any particulate matter settling within the lower portion of that chamber is masked from exposure to the light and would not be expected to alter the test results.

The results converted to digital form are automatically imprinted by a conventional printer (not shown) to the lower data-receiving tab portion of the pack and, immediately following the application of such data, the pack is advanced to a cutting station (FIG. 16) where the lower card or tab portion is separated from the remainder of the pack along severance line 27.

While in the foregoing we have disclosed an embodiment of the invention in considerable detail for purposes of illustration, it will be understood by those skilled in the art that many of these details may be varied without departing from the spirit and scope of the invention.

We claim:

1. A test pack for use in reacting a sample of body fluid with a test reagent, comprising a resilient, opaque, preformed, piercable, deformable and shape-recoverable panel secured to one side of a relatively rigid transparent panel and defining at least one reaction chamber therebetween, said reaction chamber having a planar transparent wall portion provided by said relatively rigid panel and having an opposing resilient wall portion provided by said resilient panel, said resilient wall portion of said reaction chamber being capable of being flexed inwardly by external force into a deformed condition of stress in which the volume of said chamber is reduced and a returning to its original configuration upon removal of said force to relieve said stress, and a test reagent disposed within said reaction chamber.

2. The test pack of claim 1 in which said resilient wall of said reaction chamber is normally of convex horizontal cross-sectional configuration.

3. The test pack of claim 2 in which said reaction chamber is of generally semi-cylindrical configuration.

4. The test pack of claim 1 in which said rigid transparent panel is substantially planar throughout its entire extent.

5. The test pack of claim 1 in which said resilient wall portion of said reaction chamber is normally generally semi-cylindrical in configuration, said generally semicylindrical wall portion being longitudinally elongated and is provided at least at one end thereof with a piercable end wall extending generally normal to the longitudinal axis of said chamber.

6. The test pack of claim 1 in which said reagent is normally disposed in said reaction chamber in solid form.

7. The test pack of claim 1 in which said pack is generally rectangular in configuration, said pack being provided with a pair of integral ear portions projecting outwardly adjacent corners on opposite sides thereof for suspending said pack in generally vertical conditions.

8. The test pack of claim 7 in which said ear portions are of unequal size.

9. A test pack for simultaneously performing a series of different clinical tests upon dilutions of a single sample of body fluid, comprising a relatively rigid transparent panel and a resilient opaque panel joined together and defining a plurality of preformed sealed reaction chambers therebetween; said reaction chambers containing measured quantities of different reagents capable of reacting with dilutions of a sample of body fluid to produce fluorescent reaction products, the extent of such fluorescence being representative of the intensity of each reaction; said reaction chambers each having a planar transparent wall portion provided by said relatively rigid panel and having an opposing resilient wall portion of generally convex cross-sectional configuration provided by said resilient panel; said resilient wall portion of each reaction chamber being capable of being flexed inwardly by external force into a stressed concave configuration, and of returning by reason of such stress into its original convex configuration when said external force is withdrawn, for mixing the reagents of said reaction chambers with dilutions of a sample of body fluid injected into said chambers.

10. The test pack of claim 9 in which said resilient wall portion of each reaction chamber is normally of generally semi-cylindrical configuration.

11. The test pack of claim 10 in which said semi-cylindrical wall portion is axially elongated and is provided at least at one end thereof with an integral end wall extending normal to the longitudinal axis of said chamber.

12. The test pack of claim 9 in which said relatively rigid transparent panel is substantially planar throughout its entire extent.

13. The structure of claim 9 in which said pack is generally rectangular in configuration and is provided with a pair of ear portions projecting outwardly from adjacent corners for the suspension of said pack thereby.

14. The structure of claim 13 in which said ear portions are of unequal size.

15. A method for reacting a diluted sample of body fluid with a test reagent capable of reacting with said fluid to produce a fluorescent reaction product, comprising the steps of partially filling a vertically-elongated chamber containing a test reagent with a diluted sample of body fluid, said chamber having one planar and transparent side wall and having a semi-rigid, opaque, and normally generally semi-cylindrical opposing side wall, bracing said planar side wall against a heated first platen and then advancing a second platen into engagement with a lower portion of said semi-rigid side wall to stress the same and reduce the volume of the chamber's lower portion, said semi-rigid side wall being capable of returning by reason of said stress to its original semi-cylindrical condition when said second platen is withdrawn, then withdrawing said second platen so that the lower portion of said semi-rigid wall returns to its normal semi-cylindrical configuration to relieve said stress, and repeating said advancing and withdrawing steps to mix thoroughly the contents of said chamber while maintaining the same at a preselected reaction temperature, and thereafter directing a beam of ultraviolet light obliquely through said planar transparent wall and measuring the intensity of the fluorescence emitted by the reaction product back through said planar transparent wall.

16. The method of claim 15 in which said second platen is heated.

17. The method of claim 15 in which said light-directing step is performed while said planar wall is braced by a second heated platen and said semi-rigid wall is held inwardly by said platen in a configuration smoothly of reversed curvature.

18. An apparatus for use in performing and measuring test reactions on body fluids, each said reaction being performed in a test pack having an opaque preformed semi-rigid panel secured to one side of a transparent and relatively flat rigid panel to define at least one vertically-elongated reaction chamber therebetween, said reaction chamber having a planar transparent wall portion provided by said rigid panel and an opposing semi-rigid semi-cylindrical wall portion capable of being flexed inwardly by external force, wherein the improvement comprises support means for suspending said pack in a substantially vertical plane with said elongated reaction chamber extending in a vertical direction, first platen means providing a heated planar surface disposed against said rigid panel, second platen means provided a heated arcuate surface engagable with the semi-rigid wall portion of said chamber, means mounting said first and second platen means for relative movement towards and away from each other, said arcuate surface of said second platen means having a convex curvature in a horizontal plane for reversing the curvature of said semi-cylindrical wall portion when said pack is compressed between said platen means.

19. The apparatus of claim 18 in which said convex curvature of said arcuate surface is of shorter radius than the curvature of said generally semi-cylindrical wall portion.

20. The apparatus of claim 19 in which a light passage is provided in said first platen means, means for directing a beam of ultraviolet light through said passage and at an oblique angle toward the transparent wall portion of said reaction chamber, and means for measuring the fluorescence resulting from the irradiation of the contents of said reaction chamber with said ultraviolet light.

* * * * *